United States Patent
Ayers (10) Patent No.: US 10,662,513 B2
(45) Date of Patent: May 26, 2020

(54) DYNAMIC, NON-HOMOGENOUS SHAPE MEMORY ALLOYS

(71) Applicant: Verkko Biomedical, LLC, Aurora, CO (US)

(72) Inventor: Reed A Ayers, Arvada, CO (US)

(73) Assignee: Verkko Biomedical, LLC, Aurora, CO (US)

( * ) Notice: Subject to any disclaimer, the term of this patent is extended or adjusted under 35 U.S.C. 154(b) by 213 days.

(21) Appl. No.: 15/659,369

(22) Filed: Jul. 25, 2017

(65) Prior Publication Data
US 2018/0030580 A1 Feb. 1, 2018

Related U.S. Application Data

(60) Provisional application No. 62/366,837, filed on Jul. 26, 2016.

(51) Int. Cl.
| | |
|---|---|
| *B22F 3/105* | (2006.01) |
| *C22F 1/00* | (2006.01) |
| *C22C 19/03* | (2006.01) |
| *C22C 14/00* | (2006.01) |
| *C22C 1/04* | (2006.01) |
| *A61L 27/00* | (2006.01) |

(Continued)

(52) U.S. Cl.
CPC .............. *C22F 1/006* (2013.01); *A61B 17/00* (2013.01); *A61B 17/7002* (2013.01); *A61B 17/72* (2013.01); *A61B 17/80* (2013.01); *A61L 27/00* (2013.01); *A61L 27/06* (2013.01); *A61L 27/306* (2013.01); *B22F 3/105* (2013.01); *B22F 3/1055* (2013.01); *B22F 7/06* (2013.01); *B33Y 10/00* (2014.12); *B33Y 70/00* (2014.12); *C22C 1/0433* (2013.01); *C22C 1/0458* (2013.01); *C22C 14/00* (2013.01); *C22C 19/03* (2013.01); *A61B 2017/00526* (2013.01); *A61B 2017/00867* (2013.01); *B33Y 80/00* (2014.12); *C21D 2201/01* (2013.01); *Y02P 10/295* (2015.11)

(58) Field of Classification Search
None
See application file for complete search history.

(56) References Cited

U.S. PATENT DOCUMENTS

| | | |
|---|---|---|
| 6,092,530 A | 7/2000 | Weissman et al. |
| 6,206,835 B1 | 3/2001 | Spillman, Jr. et al. |

(Continued)

FOREIGN PATENT DOCUMENTS

| | | |
|---|---|---|
| RU | 2218242 C2 * | 12/2003 |
| WO | WO-2015//112365 A1 * | 7/2015 |

OTHER PUBLICATIONS

"Verfahren and Vorrichtung zum Herstellen dreidimensionaler Gegenstande", Research Disclosure database No. 576003, published Apr. 2012.*

(Continued)

*Primary Examiner* — George Wyszomierski
(74) *Attorney, Agent, or Firm* — Elevated IP, LLC (57) ABSTRACT

Composite alloys comprising a first alloy portion comprising nickel and titanium and a second alloy portion comprising nickel and titanium in a different stoichiometry than the first alloy portion are disclosed, along with related methods of manufacture and use. Particularly, the composite alloys may be used in customized medical devices where a shape memory effect would be beneficial.

17 Claims, 4 Drawing Sheets

(51) Int. Cl.
    *A61L 27/06*     (2006.01)
    *B33Y 70/00*     (2020.01)
    *A61B 17/70*     (2006.01)
    *B22F 7/06*     (2006.01)
    *A61B 17/80*     (2006.01)
    *A61L 27/30*     (2006.01)
    *A61B 17/00*     (2006.01)
    *B33Y 10/00*     (2015.01)
    *A61B 17/72*     (2006.01)
    *B33Y 80/00*     (2015.01)

(56) References Cited

U.S. PATENT DOCUMENTS

| | | |
|---|---|---|
| 6,248,649 B1 | 6/2001 | Henley et al. |
| 6,330,885 B1 | 12/2001 | Weissman et al. |
| 6,444,487 B1 | 9/2002 | Boggs et al. |
| 6,458,723 B1 | 10/2002 | Henley et al. |
| 6,480,730 B2 | 11/2002 | Darrow et al. |
| 6,486,008 B1 | 11/2002 | Lee |
| 8,545,786 B2 | 10/2013 | Ayers et al. |
| 2004/0083611 A1* | 5/2004 | Rubbert .......... A61C 7/20 29/896.11 |
| 2011/0106290 A1* | 5/2011 | Hovel .......... B22F 3/1055 700/120 |
| 2012/0177810 A1* | 7/2012 | Mazumder .......... G01N 21/718 427/8 |
| 2014/0212320 A1 | 7/2014 | Ayers |
| 2014/0335197 A1 | 11/2014 | Ayers et al. |
| 2015/0335785 A1 | 11/2015 | Ayers |
| 2017/0173688 A1* | 6/2017 | Miyashita .......... B29C 64/165 |

OTHER PUBLICATIONS

Ayers et al., "Combustion Synthesis of Porous Biomaterials", (Dec. 22, 2006), J. Biomed. Mater. Res. Part A, 634-643.

Castillo et al., "Effects of Gravity on Combustion Synthesis of Functionally Graded Biomaterials", (2003), Adv. Space Res., 265-270, vol. 32, No. 2.

Duerig, "NiTi Alloys by Powder Metallurgical Methods", Proceedings of the First Int'l Conference on Shape Memory and Superplastic Technologies, (1994), pp. 31-36.

Szurman and Kursa, "Methods for Ni—Ti Based Alloys Preparation and Their Comparison", Metal 2010, (2010).

\* cited by examiner

DYNAMIC, NON-HOMOGENOUS SHAPE MEMORY ALLOYS

CROSS-REFERENCE TO RELATED APPLICATIONS

This application claims the benefit of and priority to U.S. Provisional Patent Application No. 62/366,837, filed Jul. 26, 2016, which is hereby incorporated by reference in its entirety.

STATEMENT REGARDING GOVERNMENT FUNDING

None.

BACKGROUND

In orthopedic spinal procedures requiring the use of stabilizing or bone affecting instrumentation to correct deformities such as scoliosis, to treat trauma, or to achieve fusion, the use of rigid or stiff instrumentation is the current standard of care. This instrumentation, however, has many limitations.

First, it is difficult to use due to inherent stiffness, where the rods have to be rigid enough to hold the weight and deforming forces of a patient's spine in three-dimensional space. This level of rigidity makes it difficult to intricately contour the rods to fit the patient's anatomy.

Second, the rigidity of the rods limits the correction of a spine to that which can be achieved acutely in the short duration of an operation. The spine is a living, dynamic system that could potentially deform over longer periods of time compared to the brief time allowed in the operating room. Thus, if continuous forces could be applied for longer periods of time, greater correction could be obtained.

Third, spine constructs are often "over-engineered", which can result in stress shielding (a reduction in bone density due to reduced physiological responses to impact) and/or adjacent level degeneration. Further, the existence or development of screw-rod-bone mismatches in rigidity can lead to bone failure (fracture).

Fourth, since instrumentation systems (rods and screws combined) are rigid and cannot tolerate many cycles of strain relative to the life of the patient, fusion of the spine is required. Thus, spines that perhaps could be treated with motion-preserving techniques currently require fusion to correct curvature.

SUMMARY

Shape memory alloy (SMA) instrumentation may address the clinical challenges outlined above. For example, SMAs slowly revert to an original shape, which addresses the time constraints previously mentioned and may allow continued physiologic motion while applying a deformity-correcting force over a duration of 1-5 years. The instrumentation can also be converted to a ductile phase in the operating theater when warmed and implanted in order to have the ability to customize rods to fit a patient's biomechanical needs, even when stiffer devices are used for heavier patients or for more inherently unstable constructs.

Methods and devices comprising composite alloys that a surgeon can shape into a medical device in the operating room and then implant into a patient during surgery are provided herein. These devices mimic the bone mechanics more appropriately than existing materials, and they can be trained to move bone as dictated by the patient's physiology, reducing the need for staged surgeries.

In an embodiment, a medical device, such as a spine rod, is comprised of a NiTi metal alloy that has at least two portions with different compositions that are adjacent and interconnected through a functional gradient interface. Additional metals may be included in the NiTi alloy. In an embodiment, the at least two portions of the alloy may have different physical and/or chemical properties, such as yield strength, tensile strength, Young's modulus, transition temperature, oxidation susceptibility, phase ratios, elemental stoichiometry, intermetallic content, and density, e.g., due to different compositions and/or different porosities. The incorporation of various alloy compositions, densities, and porosities within a single device, and in a predetermined 3D layout, makes it possible to customize medical devices made of the composite alloys to meet a patient's biomedical needs.

In an aspect, a method of producing a composite alloy comprises: depositing a non-uniform powder layer onto a surface, wherein the non-uniform powder layer comprises a first portion having a first composition of at least nickel (Ni) and titanium (Ti) and a second portion having a second composition of at least Ni and Ti, wherein the first and second compositions are different, the first portion is received at a first location of the surface and the second portion is received at a second location of the surface, and the first and second locations are different; applying energy from an energy source to the non-uniform powder layer substantially concurrently with the depositing, wherein the energy application forms a substantially contiguous layer of the composite alloy comprising a first alloy portion having the first composition at the first location on the surface and a second alloy portion having the second composition at the second location on the surface; and repeating the depositing and applying steps to form a body having a first desired shape comprising at least the first and second alloy portions. In an embodiment, a method of producing a composite alloy further comprises a step of thermo-mechanically training the composite alloy.

In an aspect, a composite alloy comprises a first alloy portion comprising a first composition of 45 to 55 wt. % nickel (Ni) and 45 to 55 wt. % titanium (Ti) and a second alloy portion comprising a second composition of 45 to 55 wt. % nickel (Ni) and 45 to 55 wt. % titanium (Ti); wherein the first and the second compositions are different; and wherein the first alloy portion and the second alloy portion are adjacent and interconnected through a functional gradient interface. In an embodiment, the first and the second compositions are stoichiometrically different.

In an embodiment, the composite alloy further comprises a third alloy portion comprising a third composition, wherein the third alloy portion is adjacent and interconnected through a functional gradient interface with the first alloy portion and/or the second alloy portion.

In an embodiment, a functional gradient interface is predominantly oriented along a longitudinal axis of the composite alloy or is predominantly oriented along a lateral axis of the composite alloy. In an embodiment, a functional gradient interface is non-linear.

In an embodiment, a composite alloy is formed into a medical device. For example, the medical device may be selected from the group consisting of an implantable spine rod, an external medical brace, a component of an external medical brace, a bone plate, a screw, an intramedullary nail, a vertebral space and a pin. In an embodiment, the medical device is an implantable spine rod.

In an embodiment, the density of the first alloy portion is between 30% and 100% of theoretical maximum density for the first alloy, and the density of the second alloy portion is between 30% and 100% of theoretical maximum density for the second alloy.

In an embodiment, the first alloy portion and the second alloy portion occupy first and second locations respectively. In an embodiment, the first location and the second location are predetermined. In an embodiment, the first and second locations are distributed non-uniformly throughout the composite alloy.

In an embodiment, the first and second compositions each comprise 45 wt. % to 55 wt. % Ni and 45 wt. % to 55 wt. % Ti.

In an embodiment, the first and/or the second composition(s) further comprise(s) up to 10 wt. %, or up to 8 wt. %, or up to 5 wt. % of at least one element selected from the group consisting of zirconium (Zr), aluminum (Al), niobium (Nb), vanadium (V), copper (Cu), iron (Fe) and combinations thereof.

In an embodiment, the first and/or the second composition(s) comprise(s) 0 wt. % to 2 wt. %, or 0.01 wt. % to 2 wt. %, or 0.02 wt. % to 1.8 wt. %, or 0.05 wt. % to 1.5 wt. %, or 0.08 wt. % to 1.3 wt. % of at least one element selected from the group consisting of Zr, Al, Nb, V, Cu, Fe and combinations thereof.

In an embodiment, the powder layer comprises powder particles having a mean diameter between 1,000 nm and 100,000 nm, or between 1,000 nm and 50,000 nm, or between 1,000 nm and 10,000 nm, or between 1,000 nm and 5,000 nm, or between 1,000 nm and 4,400 nm.

In an embodiment, a porosity of the first alloy portion and/or the second alloy portion is between 0% and 70%, or between 0.5% and 70%, or between 25% and 70%, or between 50% and 65% on the basis of image analysis or Archimedes principle.

In an embodiment, the first alloy is a superelastic alloy and the second alloy is a shape memory alloy, or the first alloy is a superelastic alloy and the second alloy is a different superelastic alloy, or the first alloy is a shape memory alloy and the second alloy is a different shape memory alloy. In an embodiment, a composite alloy may be 0-100% superelastic, 0-100% shape memory alloy, or any combination thereof.

In an embodiment, the composite alloy is trained to undergo a transition from a first desired shape to a second desired shape. For example, one or more portions of a composite alloy may transition from a martensite phase to an austenite phase. In an embodiment, the total strain in tension, compression, torsion or combinations thereof experienced by the composite alloy over the course of the transition is less than 0.2, or less than 0.1, or less than 0.05. In an embodiment, the rate of strain experienced by the composite alloy over the course of the transition is less than 2000µε/day, or less than 1500µε/day, or less than 1000µε/day, or less than 500µε/day. In an embodiment, a composite alloy has a non-uniform strain response throughout its bulk.

In an embodiment, a method of producing a composite alloy further comprises a step of coating the composite alloy with a coating. For example, the coating may be selected from the group consisting of a metal, a metal alloy, a ceramic, a polymer, titanium hydroxide (Ti(OH)$_2$), titanium hydride (TiH$_2$), titanium nitride (TiN), titanium dioxide (TiO$_2$), collagen, bone morphogenic proteins and combinations thereof. Suitable metals for the coating include but are not limited to biocompatible metals, such as gold, silver and platinum.

In an embodiment, an energy source comprises a coherent radiation source, a thermal heat source, an electrical energy source, or any combination thereof. In an embodiment, the energy source is an electrical energy source and the step of applying energy comprises spark plasma sintering. In an embodiment, the energy source is a coherent radiation source and the step of applying energy comprises condensed-phase combustion synthesis.

In an embodiment, each of the first and second compositions has a heat of combustion of at least 350 joules per gram.

In an embodiment, a non-equilibrium process is used to fabricate a composite alloy comprising a variety of compositions, densities, and porosities within a single unitary body, such as a medical device. The distribution of the compositions, densities, and porosities within the unitary body is tailored to fit a patient's biomedical needs.

In an embodiment, the composite alloy comprises a shape memory alloy capable of transitioning from a first desired shape to a second desired shape under a selected stimulus. In an embodiment, the first desired shape is a spinal rod characterized by matching the patient conformation at the time of surgery and the second desired shape is a spinal rod characterized by a shape change to a desired conformation as deemed necessary by the treating surgeon to correct the deformity or provide patient balance. In an embodiment, the first desired shape is a shape that substantially conforms to a patient's anatomy at the time of surgery and the second desired shape is a shape more closely approximating an ideal anatomical shape. In an embodiment, the first desired shape is a shape that substantially conforms to a patient's anatomy at the time of surgery and the second desired shape is a substantially ideal anatomical shape.

In an embodiment, the selected stimulus is thermal energy. In an embodiment, the thermal energy raises the temperature of the first and/or the second alloy between 0° C. and 1,000° C., or between 1° C. and 850° C., or between 5° C. and 600° C. In an embodiment, the thermal energy is between 0 Watts and 2000 Watts, or between 0.5 Watts and 1500 Watts, or between 5 Watts and 1000 Watts, or between 50 Watts and 500 Watts.

STATEMENTS REGARDING CHEMICAL COMPOUNDS AND NOMENCLATURE

In an embodiment, an alloy, a composition or compound of the invention is isolated or purified. In an embodiment, an isolated or purified compound is at least partially isolated or purified as would be understood in the art. In an embodiment, an alloy, composition or compound of the invention has a chemical purity of at least 95%, optionally for some applications at least 99%, optionally for some applications at least 99.9%, optionally for some applications at least 99.99%, and optionally for some applications at least 99.999%.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of this description.

"Alloy" refers to a material of two or more metals, or of a metal and another material. For example, brass is an alloy of copper and zinc; steel is an alloy of iron and carbon.

A "composite alloy" refers to unitary body comprising two or more alloys, or an alloy and another material.

A "construct" is an object built from various parts. In an embodiment, a composite alloy is a construct.

"Composition" refers to the quantitative relationships among elements in compounds.

"Shape memory alloy (SMA)" refers to a unique class of metal alloys that can recover apparent permanent strains when they are heated above a certain temperature (transition temperature). The SMAs have two stable phases—the high-temperature phase, called austenite, and the low-temperature phase, called martensite. An SMA is an alloy that "remembers" its original shape and when deformed returns to its pre-deformed shape when heated.

"Training" refers to the process of cycling an SMA through heating and cooling cycles while mechanically constraining the alloy in order to predispose the alloy to adopt a particular desired shape when it undergoes a phase transformation.

A "green body" or "green construct" refers to a precursor of a final product. For example, a final product may be achieved by heating, combusting, sintering and/or shaping a green construct. In an embodiment, a green construct may be a compressed powder formation having the stoichiometry, 3D layout, and general dimensions of a desired composite alloy.

"Spark plasma sintering (SPS)", also known as field assisted sintering technique (FAST) or pulsed electric current sintering (PECS), is a sintering technique. The main characteristic of SPS is that a pulsed DC current directly passes through a graphite die, as well as a powder compact (green construct) in cases of conductive samples.

"Condensed-phase combustion synthesis" refers to Combustion Synthesis (CS) which can occur by two modes: self-propagating high-temperature synthesis (SHS) and volume combustion synthesis (VCS). In both cases, reactants may be pressed into a pellet (green construct), typically cylindrical in shape. The samples are then heated by an external source (e.g., tungsten coil, laser) either locally (SHS) or uniformly (VCS) to initiate an exothermic reaction.

"Superelasticity" refers to an elastic (reversible) response to an applied stress triggering a phase transformation between the austenite and martensite phases of a crystal.

"Porosity" refers to the ratio, expressed as a percentage, of the volume of the pores or interstices of a substance, such as an alloy or green construct, to the total volume of the mass.

"Archimedes principle" refers to the upward buoyant force that is exerted on a body immersed in a fluid, whether fully or partially submerged. The force is equal to the weight of the fluid that the body displaces.

A "functional gradient interface" is an area of transition between a first composition and a second composition characterized by a spatial variation in composition and/or structure. Materials comprising one or more functional gradient interfaces generally do not have distinct crystallographic boundaries or domains.

"Proximal" and "distal" refer to the relative positions of two or more objects, planes or surfaces. For example, an object that is close in space to a reference point relative to the position of another object is considered proximal to the reference point, whereas an object that is further away in space from a reference point relative to the position of another object is considered distal to the reference point.

"3-D printing" refers to an additive manufacturing process that may be used to produce three-dimensional, complex objects, layer-by-layer, often without molds or dies.

A "predetermined" location refers to the position of an object, plane, surface or material within a construct that is set or determined prior to fabrication and achieved during fabrication.

The terms "direct and indirect" describe the actions or physical positions of one component relative to another component. For example, a component that "directly" acts upon or touches another component does so without intervention from an intermediary. Contrarily, a component that "indirectly" acts upon or touches another component does so through an intermediary (e.g.; a third component).

"Contiguous" refers to materials or layers that are touching or connected throughout in an unbroken sequence.

"Non-uniform" refers to an inconstant, varying, irregular or non-homogeneous distribution.

Processing Techniques

NiTi has long been investigated as an alloy for biomedical applications, with several products currently on the market. However, current processing of NiTi SMA metals is based on equilibrium processes such as vacuum arc melting, vacuum induction melting and electron beam melting generating homogenous material that has a consistent strain response throughout the entire bulk. (Duerig 1994, Szurman and Miroslav 2010.) These processes are intended to generate a homogenous bulk.

Disclosed herein is the creation and use of non-equilibrium processing techniques to generate NiTi alloys having non-uniform densities and/or porosities for use in medical procedures, such as spinal reconstructions. The non-uniform material properties are generated by the specific design of material composition at specific sites within the green construct. For example, a Ti-rich region (superelastic) can be created by including an excess of Ti particles in a specified zone next to a Ni-rich region (shape memory) where the stoichiometry has more Ni particles present. Stoichiometry can also be modified by the addition of other alloying elements such as Zr, Al, Nb, V, Cu, and/or Fe. Each alloying element has a specific effect on the subsequent material properties due to modification of the material microstructure.

Composite alloys of the medical devices disclosed herein are fabricated layer-by-layer to tailor the compositions, densities, and porosities within a single device to meet a patient's biomedical needs. Suitable fabrication processes include combustion synthesis with mechanical construction of the reacting volume (consolidation) during reaction, direct metal laser sintering (DMLS) and spark plasma sintering (SPS). These processes rely on the solid-state reaction at the interfaces between elemental particles in a green body. In these cases no large volume of molten material is developed. The processes can be accommodated/enhanced by 3D laser printing technology, e.g., the laser initiates a SHS reaction to form the metal as the device is printed.

To generate a layer of homogeneous material within a composite alloy, a single type of powder is placed in a 3D printer and all laser parameters are kept constant. If a preheat is needed to effect combustion, which is common when a mixture is Ti-rich, the laser is rastered across the surface of the powder at a reduced power density (e.g., by increasing spot diameter, operating at a fast raster rate or lowering power output of the laser) to preheat the powder to a target temperature of about 350° C. to 400° C.

For SPS production of a non-homogeneous material, powders are placed or packed and axially or isostatically pressed into a green construct. Loose packed powders are processed in a graphite die, while compressed powders can be processed in a graphite die or with no die (open die). Current up to 10,000 amps at 0-10 V is passed through the green construct and/or die to affect current aided diffusion between powder particles. Process temperatures can range from 100° C. to 600° C. for 10 minutes to 120 minutes to achieve the desired microstructure, Alloy "training" is subsequently performed in an annealing oven, if necessary.

In addition to compositional variation, porosity can be used to affect material properties based on the rule of mixtures. Porosity of the composite alloys disclosed herein is generally controlled by use of a printer having a minimum pore size of about 100 μm.

Spine rods created by the present fabrication processes are typically 4 mm to 6 mm in diameter and 50 mm to 400 mm in length. The ends of a spine rod according to the present invention may be porous in a region 1-2 vertebral levels beyond fusion to reduce strength and stiffness, thereby reducing proximal junction kyphosis/proximal junction failure (PJK/PJF).

Figure 1:
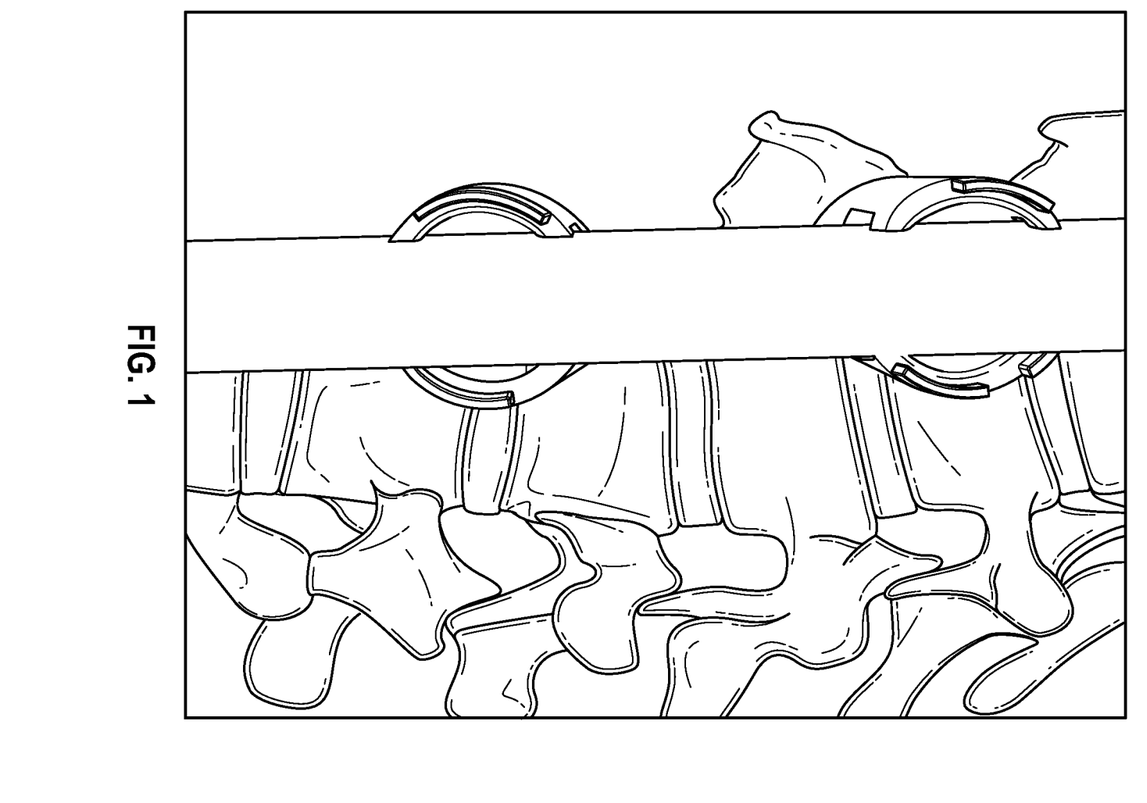
FIG. 1 provides a photograph of a 3D-printed NiTi spine rod placed in a cadaver spine, according to an exemplary embodiment.
Figure 2:
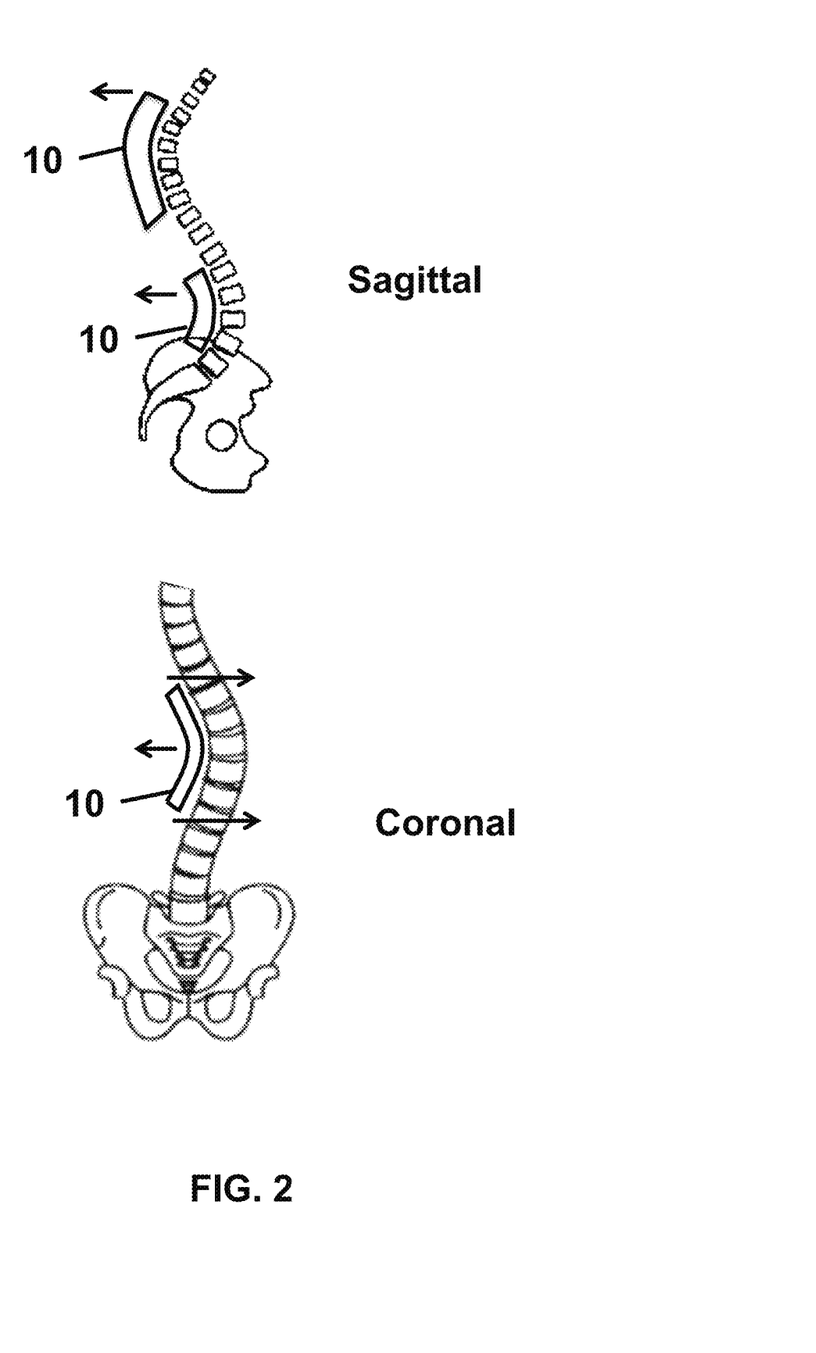
FIG. 2 provides schematic sagittal and coronal views of a hip and a spine receiving corrective forces (arrows) from one or more dynamic, composite alloy spine rods, according to the present invention.
Figure 3:
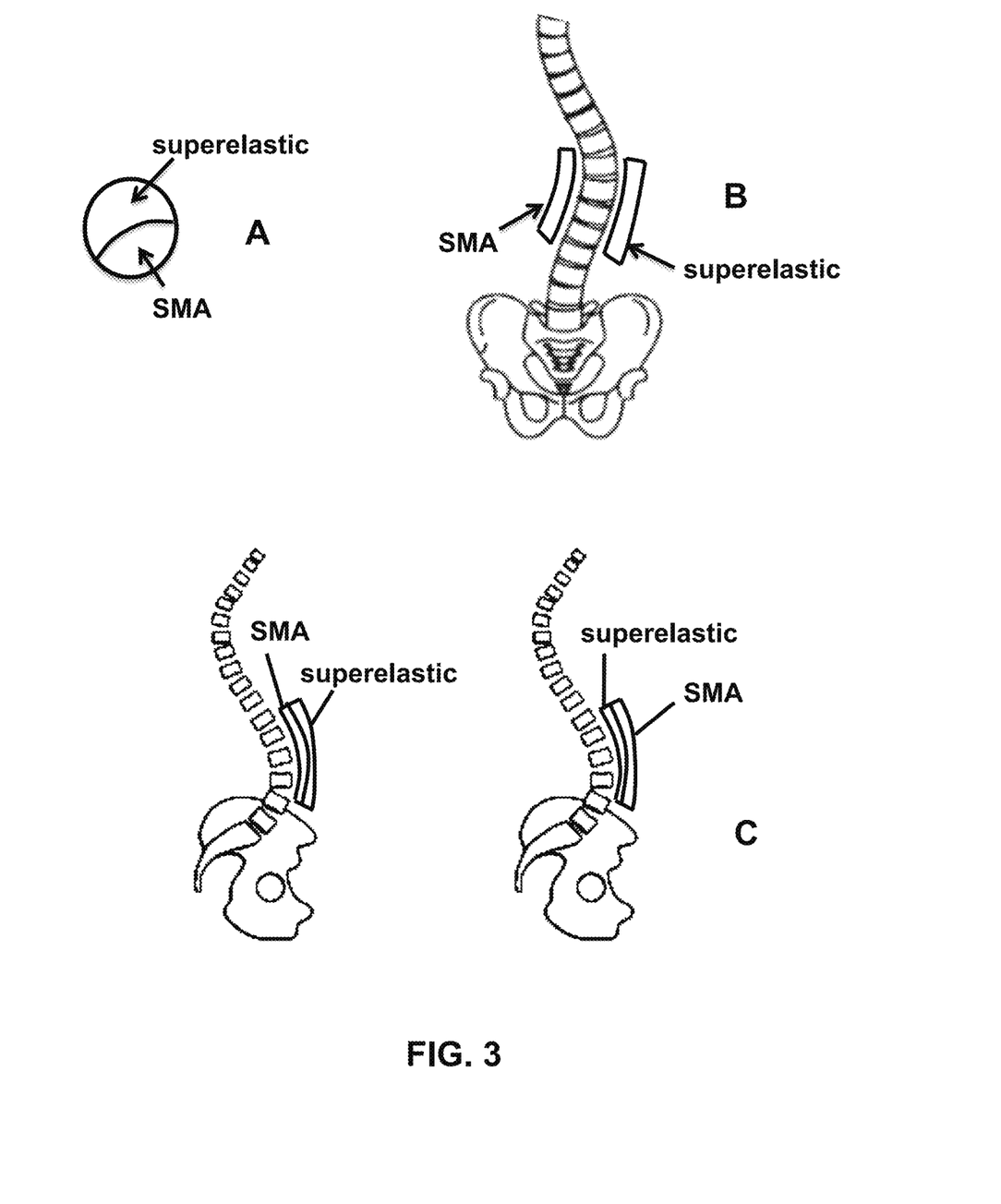
FIG. 3 provides schematic views of an exemplary composite alloy spine rod in lateral cross-section (A), as well as a sagittal view of a spine with a shape memory alloy (SMA) on one side of the spine and a superelastic alloy on the other side of the spine (B) and coronal views of a spine with a composite alloy having a SMA portion proximal to the spine and a superelastic portion distal from the spine or, alternatively, a superelastic portion proximal to the spine and a SMA distal from the spine (C), according to multiple embodiments.
Figure 4:
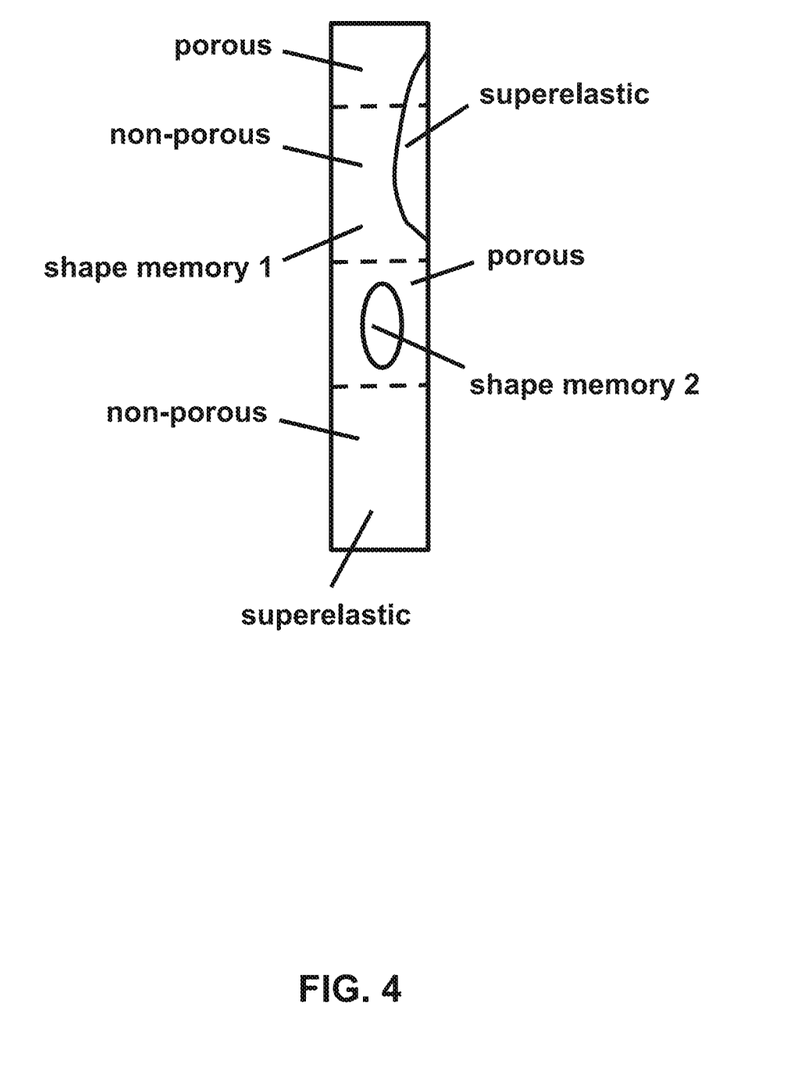
FIG. 4 provides a schematic diagram of a spine rod illustrating different types of alloys formed into a single, composite body, according to an embodiment.

Examples of the composite alloys and medical devices are illustrated in the accompanying figures. FIG. 1 provides a photograph of a 3D printed NiTi spine rod placed in a cadaver spine. FIG. 2 provides schematic sagittal and coronal views of a hip and a spine receiving corrective forces (arrows) from one or more dynamic spine rods 10. FIG. 3 provides schematic views of an exemplary composite spine rod in lateral cross-section (A), as well as a sagittal view of a spine with a shape memory alloy (SMA) on one side of the spine and a superelastic alloy on the other side of the spine (B) and coronal views of a spine with a composite alloy having a SMA portion proximal to the spine and a superelastic portion distal from the spine or, alternatively, a superelastic portion proximal to the spine and a SMA distal from the spine (C). FIG. 4 provides a schematic diagram of a spine rod illustrating different types of alloys formed into a single, composite body, according to an embodiment.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps. All art-known functional equivalents of materials and methods are intended to be included in this disclosure.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

It must be noted that as used herein and in the appended claims, the singular forms "a", "an", and "the" include plural reference unless the context clearly dictates otherwise. Thus, for example, reference to "a rod" includes a plurality of such rods and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

What is claimed is:

1. A method of producing a composite alloy, comprising:
   depositing a non-uniform powder layer onto a surface, wherein said non-uniform powder layer comprises:
      a first portion having a first composition of at least nickel (Ni) and titanium (Ti); and
      a second portion having a second composition of at least Ni and Ti, wherein the first and second compositions are different;
   wherein the first portion is received at a first location of the surface and the second portion is received at a second location of the surface, wherein the first and second locations are different;
   applying energy from an energy source to the non-uniform powder layer substantially concurrently with said depositing, wherein said energy application forms a substantially contiguous layer of the composite alloy comprising:
      a first alloy portion having the first composition at the first location on the surface; and
      a second alloy portion having the second composition at the second location on the surface;
      wherein at least one of the first alloy and the second alloy is a shape memory alloy; and
   repeating said depositing and applying steps to form a body having a first desired shape comprising at least the first and second alloy portions.

2. The method of claim 1, wherein said first and second compositions each comprise 45 wt. % to 55 wt. % Ni and 45 wt. % to 55 wt. % Ti.

3. The method of claim 2, wherein said first and/or said second composition(s) further comprise(s) up to 10 wt. % of at least one element selected from the group consisting of zirconium (Zr), aluminum (Al), niobium (Nb), vanadium (V), copper (Cu), iron (Fe) and combinations thereof.

4. The method of claim 2, wherein said first and/or said second composition(s) comprise(s) 0 wt. % to 2 wt. % of at least one element selected from the group consisting of Zr, Al, Nb, V, Cu, Fe and combinations thereof.

5. The method of claim 1, wherein said powder layer comprises powder particles having a mean diameter between 1,000 nm and 100,000 nm.

6. The method of claim 1, wherein a porosity of said first alloy portion and/or said second alloy portion is between 0% and 70% on the basis of image analysis or Archimedes principle.

7. The method of claim 1, wherein said first alloy is a superelastic alloy and said second alloy is a shape memory alloy, or wherein said first alloy is a shape memory alloy and said second alloy is a different shape memory alloy.

8. The method of claim 1, further comprising a step of thermo-mechanically training the composite alloy.

9. The method of claim 8, wherein said step of thermo-mechanically training the composite alloy comprises forcing the composite alloy to undergo a transition from a first desired shape to a second desired shape.

10. The method of claim 9, wherein the total strain experienced by the composite alloy over the course of the transition is less than 0.2.

11. The method of claim 9, wherein the rate of strain experienced by the composite alloy over the course of the transition is less than 2000µε/day.

12. The method of claim 1, wherein said first alloy portion and said second alloy portion are adjacent and interconnected through a functional gradient interface.

13. The method of claim 1, wherein said body is a medical device selected from the group consisting of an implantable spine rod, an external medical brace, a component of an external medical brace, a bone plate, a screw, an intramedullary nail, a vertebral space and a pin.

14. The method of claim 1, wherein said step of applying energy triggers a condensed-phase combustion synthesis reaction.

15. The method of claim 14, wherein the condensed-phase combustion synthesis reaction is selected from the group consisting of self-propagating high-temperature synthesis (SHS), volume combustion synthesis (VCS), direct metal laser sintering (DMLS), spark plasma sintering (SPS) and 3D laser printing.

16. The method of claim 1, further comprising a step of coating the composite alloy with a coating.

17. The method of claim 16, wherein the coating is selected from the group consisting of a metal, a metal alloy, a ceramic, a polymer, titanium hydroxide (Ti(OH)$_2$), titanium hydride (TiH$_2$), titanium nitride (TiN), titanium dioxide (TiO$_2$), collagen, bone morphogenic proteins and combinations thereof.

* * * * *